United States Patent [19]
McGonigle et al.

[11] Patent Number: 6,054,638
[45] Date of Patent: Apr. 25, 2000

[54] SOYBEAN ADP RIBOSYLATION FACTOR

[75] Inventors: Brian McGonigle, Wilmington, Del.; Daniel P. O'Keefe, Ridley Park, Pa.

[73] Assignee: E. I. du Pont de Nemours and Company, Wilmington, Del.

[21] Appl. No.: 08/984,550

[22] Filed: Dec. 3, 1997

[51] Int. Cl.⁷ ............................ C12N 15/00; C12N 15/29; C12N 15/82; A01H 4/00
[52] U.S. Cl. .......................... 800/298; 800/295; 800/292; 800/287; 800/279; 800/278; 536/23.6; 536/24.1; 435/468; 435/419; 435/320.1
[58] Field of Search .................................. 800/278, 279, 800/287, 292, 295, 298; 536/23.6, 24.1; 435/468, 469, 320.1

[56] References Cited

PUBLICATIONS

S. Russ Price et al., *Molecular and Cellular Biochemistry*, 159, 15–23, 1996.
Ira I.G.S. Verwoert et al., *Plant Molecular Biology*, 27, 629–633, 1995.
Jan Szopa et al., *Plant Cell Reports*, 14, 180–183, 1994.
Matthieu Lebas et al., *Plant Physiol.*, 106, 809–810, 1994.
Farid Regad et al., *Federation of European Biochemical Socieities (FEBS)*, 316, No.2, 133–136, 1993.
Nicholas T. Ktistakis et al., *The Journal of Cell Biology*, 134, No. 2, 295–306, 1996.
Michel Franco et al., *The Journal of Biological Chemistry*, 270, No. 3, 1337–1341, 1995.
Thomas H. Sollner et al., *Cell Structure and Function*, 21, 407–412, 1996.
Tito Serafini et al., *Cell*, 67, 239–253, 1991.
Jan Szopa et al., *Plant Physiol*, 145, 383–386, 1995.
Mariano Barbacid, *Ann. Rev. Biochem.*, 56, 779–827, 1987.
Tomohiro Kiyosue et al., *Plant Cell Physiol.*, 36(5), 849–856, 1995.
Fang–Jen S. Lee et al., *The Journal of Biological Chemistry*, 269, No. 33, 20931–20937, 1994.
S. Russ Price et al., *The Journal of Biological Chemistry*, 267, No. 25, 17766–17772, 1992.
James M. Lenhard et al., *The Journal of Biological Chemistry*, 267, No. 18, 13047–13052, 1992.
Richard A. Kahn et al., *The Journal of Biological Chemistry*, 267, No. 18, 13039–13046, 1992.
James J. Murtagh, Jr. et al., *The Journal of Biological Chemistry*, 267, No. 14, 9654–9662, 1992.
Chii–Ming Lee et al., *The Journal of Biological Chemistry*, 267, No. 13, 9028–9034, 1992.
Richard A. Kahn et al., *The Journal of Biological Chemistry*, 269, No. 10, 6228–6234, 1984.
Leonard S. Schleifer et al., *The Journal of Biological Chemistry*, 257, No. 1, 20–23, 1982.
Theodore G. Gabig, *The Journal of Biological Chemistry*, 262, No. 4, 1685–1690, 1967.
Richard A. Kahn et al., *The Journal of Biological Chemistry*, 263, No. 17, 8282–8287, 1988.
Ofra Weiss et al., *The Journal of Biological Chemistry*, 264, No. 35, 21066–21072, 1989.
Su–Chen Tsai et al., *The Journal of Biological Chemistry*, 263, No. 4, 1768–1772, 1988.
Henry R. Bourne et al., *Nature*, 349, 117–127, 1991.
Jenny L. Sewell et al., *Proc. Natl. Acad. Sci. USA*, 85, 4620–4624, 1988.
Henry R. Bourne, *Cell*, 53, 669–671, 1988.
Bruno Goud et al., *Nature*, 345, 553–556, 1990.
Annette L. Bowman et al., *Nature*, 358, 512–514, 1992.
Mary W. Walker et al., The Journal of Biological Chemistry, 267, No. 5, 3230–3235, 1992.
Richard A. Kahn, *The Journal of Biological Chemistry*, 266, No. 24, 15595–15597, 1991.
Su–Chen Tsai et al., *The Journal of Biological Chemistry*, 266, No. 13, 8213–8219, 1991.
Mikako Tsuchiya et al., *The Journal of Biological Chemistry*, 266, No. 5, 2772–2777, 1991.
Richard A. Kahn et al., *The Journal of Biological Chemistry*, 266, No. 4, 2606–2614, 1991.
Nicolas Vitale et al., *The Journal of Biological Chemistry*, 272, No. 7, 2897–2904, 1997.
Tim Stearns et al., *Molecular and Cellular Biology*, 10, No. 12, 6690–6699, 1990.
Ulla G. Knaus et al., *Science*, 254, 1512–1515, 1991.
Alan Hall, *Science*, 249, 635–640, 1990.
Lucia Monaco et al., *Proc. Natl. Acad. Sci USA*, 87, 2206–2210, 1990.
Romano Regazzi et al., *Biochem. J.*, 275, 639–644, 1991.
Mikako Tsuchiya et al., *Biochemistry*, 28, 9668–9673, 1989.
David A. Bobak et al., *Biochemistry*, 29, 855–861, 1990.
Masatoshi et al., *Biochimica et Biophysica Acta*, 1034, 195–199, 1990.
Tim Stearns et al., *Proc. Natl. Acad. Sci. USA*, 87, 1238–1242, 1990.
David A. Bobak, *Proc. Natl. Acad. Sci USA*, 86, 6101–6105, 1989.
Kiyosue, T., et al, Cloning of a carrot 1–9 cDNA for a member of the family of ADP–ribosylation factors (ARFs) and characterization of the binding of nucleotides by its product after expression in *E. coli*, Plant Cell Physiol., 36, 849–856, XP002096712 Aug. 28, 1995.
Szopa, J. et al., ARF–protein antisense potato displays stable ADP–ribosylation of 40 kDa protein, *Journal of Plant Physiology*, 145 No. 3, 383–386, 1994.

*Primary Examiner*—Lynette R. F. Smith
*Assistant Examiner*—Thomas Haas

[57] ABSTRACT

This invention relates to the isolation of nucleic acid fragments from soybean that encode ADP ribosylation factor (ARF) protein. This invention also relates to nucleic acid fragments encoding proteins that are capable of conferring herbicide tolerance to chlorimuron-ethyl, a sulfonylurea herbicide. The invention encompasses genetic screens for crop protection chemicals, transgenic plants, and breeding methods.

17 Claims, No Drawings

SOYBEAN ADP RIBOSYLATION FACTOR

FIELD OF THE INVENTION

This invention is in the field of plant molecular biology. More specifically, this invention pertains to nucleic acid fragments encoding soybean adenosine diphosphate (ADP) ribosylation factors (ARFs). These proteins may be involved in the protection of plants and seeds from the damaging effects of herbicides.

BACKGROUND OF THE INVENTION

The agricultural industry seeks more effective methods of crop protection. Increasingly, attention has turned to genetic manipulation of plant proteins to create safe and more effective crop protection chemicals and herbicide-resistant plants. One area of interest is the monomeric guanine nucleotide-binding proteins of the Ras superfamily. These proteins function in a variety of cellular processes including signaling, growth, immunity and protein transport (Barbacid et al., Annu. Rev. Biochem. 56:779–828 (1987); Bourne, Cell 53:669–671 (1988); Bourne et al., Nature, London 349:117–127 (1991); Gabig et al., J. Biol. Chem. 262:1685–1690 (1987); Goud et al., Nature, London 345:553–556 (1990); Hall, Science 249:635–640 (1990); Knaus et al., Science 254:1512–1515 (1991)). Adenosine diphosphate (ADP) ribosylation factors (ARFs) constitute one family of proteins of the Ras superfamily.

ARFs are 20-kDa GTP binding proteins and were initially identified as activators required for the cholera toxin-catalyzed ADP ribosylation of $G_{S\alpha}$, the stimulatory guanine nucleotide-binding (G) protein of the adenylyl cyclase system (Schleifer et al., J. Biol. Chem. 257:20–23 (1982); Kahn et al., J. Biol. Chem. 259:6228–6234 (1984); Serventi et al., Current Topics in Microbiology and Immunology 175, pp. 43–67, Springer-Verlag, Berlin Heidelberg (1992)). In the presence of guanosine 5'-triphosphate (GTP) or a nonhydrolyzable GTP analogue, ARF serves as an allosteric activator of cholera toxin ADP-ribosyltransferase activity. ARFs have also been shown to stimulate the ADP-ribosylation of proteins unrelated to the adenylate cyclase system, simple guanidino compounds such as arginine and agmatine, as well as the auto-ADP-ribosylation of the choleragen $A_1$ peptide (Noda et al., Biochim. Biophys. Acta 1034:195–199 (1990); Tsai et al., J. Biol. Chem. 263:1768–1772 (1988); Tsai et al., Proc. Natl, Acad. Sci., USA 84:5139–5142 (1987)).

ARFs are evolutionarily well-conserved and present in all eukaryotes from Giardia to mammals (Kahn et al., J. Biol. Chem. 263:8282–8287 (1988); Murtagh et al., J. Biol. Chem. 267:9654–9662 (1992); Tsai et al., J. Biol. Chem. 266:8213–8219 (1991); Tsuchiya et al., Biochemistry 28:9668–9673 (1989); Tsuchiya et al., J. Biol. Chem. 266:2772–2777 (1991)). Thus, ARFs are believed to be critical components of vesicular trafficking pathways in eukaryotic cells (Söllner et al., Cell Struct. Funct. 21:407–412 (1996)). ARF's ability to activate phospholipase D may mediate this process. (Brown et al., Cell 75:1137–1134 (1993)). It has been proposed that following its activation by ARF, phospholipase D hydrolyzes phosphotidylcholine. The phosphatidic acid produced by this reaction facilitates formation of stable binding sites for coatomer, leading to budding of coated vesicles (Ktistakis et al., J. Cell Biol. 134:295–306 (1996)).

ARFs have been localized to the Golgi apparatus of several types of cells by immunocytochemistry (Stearns et al., Proc. Natl. Acad. Sci., USA 87:1238–1242 (1990)). ARFs are required for association of nonclathrin coat proteins with intracellular transport vesicles (Serafini et al., Cell 67:239–253 (1991)) and also appear to be critical during an early step in endocytosis as well as in nuclear vesicle fusion (Boman et al., Nature, London 358:512–514 (1992); Lenhard et al., J. Biol. Chem. 267:13047–13052 (1992)). GTP binding and hydrolysis may be involved in binding of ARF to membranes. Furthermore, the nonhydrolyzable GTP analogue guanosine 5'-[γ-thio]triphosphate ($GTP_{\gamma S}$), but not GDP or ATP, promotes the association of cytosolic ARF with Golgi (Regazzi et al., Biochem. J. 275:639–644 (1991) or phospholipid membranes (Kahn et al., J. Biol. Chem. 266:15595–15597 (1991); Walker et al., J. Biol. Chem. 267:3230–3235 (1992)).

ARFs are active in their GTP-bound forms and inactive when GDP is bound. ARFs exhibit no detectable GTPase activity. The ratio of GTP/GDP that is bound is regulated by guanine nucleotide-exchange proteins and GTPase-activating proteins (Vitale et al., J. Biol. Chem. 272:3897–3904 (1997)). Additionally, myristoylation of the protein seems to be necessary for ARF function. However, it is not clear mechanistically how myristoylation affects ARF's function although it has been suggested to facilitate nucleotide exchange and enhance phospholipid-dependent stabilization of the GTP bound form (Franco et al., J. Biol. Chem. 270:1337–1341 (1995)). Some lipids and/or detergents, e.g., SDS, cardiolipin, dimyristoylphosphatidyl-choline (DMPC)/cholate, enhance ARF activities (Bobak et al., Biochemistry 29:855–861 (1990); Noda et al., Biochim. Biophys. Acta 1034:195–199 (1990); Tsai et al., J. Biol. Chem. 263:1768–1772 (1988)).

Regardless of their mechanism of action, ARFs are thought to be essential for eukaryotic cell viability. Saccharomyces cerevisiae contains three genes encoding ARF proteins and the mutant containing the deletion of arf1/arf2 is not viable (Stearns et al., Mol. Cell. Biol. 10:6690–6699 (1990); Lee et al., J. Biol. Chem. 269:20931–20937 (1994)).

By molecular cloning from cDNA and genomic libraries, and PCR amplification of RNA transcripts, six mammalian ARFs, three yeast ARFs, and two Giardia ARFs have been identified (Bobak et al., Proc. Natl. Acad. Sci., USA 86:6101–6105 (1989); Monaco et al., Proc. Natl. Acad. Sci., USA 87:2206–2210 (1990); Murtagh et al., J. Biol. Chem. 267:9654–9662 (1992); Price et al., Proc. Natl. Acad. Sci., USA 85:5488–5491 (1988); Sewell et al., Proc. Natl. Acad. Sci., USA 85:4620–4624 (1988); Stearns et al., Mol. Cell. Biol. 10:6690–6699 (1990); Tsuchiya et al., J. Biol. Chem. 266:2772–2777 (1991)). Mammalian ARFs fall into three classes based on deduced amino acid sequences, gene structure, phylogenetic analysis and size (Lee et al., J. Biol. Chem. 267:9028–9034 (1992); Tsuchiya et al., J. Biol. Chem. 266:2772–2777 (1991)). Class I ARFs are ARFs 1–3; class II includes ARFs 4 and 5; and class III has ARFs 6. The high degree of conservation between cognate ARFs is evidence of evolutionary pressure to maintain individual identities (Price et al., Mol. Cell Biochem. 159:15–23 (1996).

Members of the ARF multigene family, when expressed as recombinant proteins in E. coli, display different phospholipid and detergent requirements (Price et al., J. Biol. Chem. 267:17766–17772 (1992)). Following synthesis in E. coli all of these ARFs had enhanced cholera toxin ADP-ribosyltransferase activity in the presence of GTP (Kahn et al., J. Biol. Chem. 266:2606–2614 (1991); Price et al., J. Biol. Chem. 267:17766–17772 (1992); Weiss et al., J. Biol. Chem. 264:21066–21072 (1989)).

In general, differences in the various mammalian ARF sequences are concentrated in the extreme amino and carboxyl portions of the proteins. Only three of seventeen amino acids including Met$_1$ and Gly$_2$, in the amino termini are identical among ARFs, and four amino acids in this region of ARFs 1–5 are missing in ARF 6 (Tsuchiya et al., *J. Biol. Chem.* 266:2772–2777 (1991)). Kahn et al. reported *J. Biol. Chem.* 267:13039–13046 (1992)) that the amino-terminal regions of ARF proteins form an α-helix and that this domain is required for membrane targeting, interaction with lipid, and ARF activity.

Even less is understood about the role of ARFs in plants, although cDNAs have been cloned from a number of plants including Arabidopsis (Regad et al., *FEBS Letters* 316:133–136 (1993); Lebas et al., *Plant Physiol.* 106:809–810 (1994)), rice (Higo et al., *Plant Science* 100:41–49 (1994)), potato (Szopa et al., *Plant Cell Reports* 14:180–183 (1994)), maize (Verwoert et al., *Plant Mol. Biol.* 27:629–633 (1995)), carrot (Kiyosue et al., *Plant and Cell Physiology* 36:849–856 (1995)), and barley (EP 681028). Antisense experiments in potato show an increase in the levels of a 40-kDa ribosylated protein and concomitant decrease in a 42-kDa protein although the function and identity of these proteins are not known (Szopa et al., *Plant Physiol.* 145:383–386 (1995)). Furthermore, no obvious morphological changes were observed in the antisense plants.

A need exists for improved crop protection methods. A method that has broad applicability for screening for candidate compounds and the production of transgenic plants would have great commercial value. No such method involving nucleic acid fragments encoding soybean adenosine diphosphate (ADP) ribosylation factors (ARF's) was previously known.

SUMMARY OF THE INVENTION

The instant invention relates to isolated nucleic acid fragments encoding all or a substantial portion of a soybean ARF protein. The isolated nucleic acid fragment encoding a soybean ARF protein is selected from the group consisting of (a) an isolated nucleic acid fragment encoding all or a substantial portion of the amino acid sequence set forth in SEQ ID NO:2; (b) an isolated nucleic acid fragment that is substantially similar to an isolated nucleic acid fragment encoding all or a substantial portion of the amino acid sequence set forth in SEQ ID NO:2; and (c) an isolated nucleic acid fragment that is complementary to (a) or (b). The instant invention also relates to isolated nucleic acid fragments comprising the coding region of a soybean ARF protein wherein the nucleotide sequence of the coding region is set forth in SEQ ID NO:3. The nucleic acid fragments and corresponding polypeptides are contained in the accompanying Sequence Listing and described in the Brief Description of the Invention.

In another embodiment, the instant invention relates to chimeric genes encoding soybean ARF protein or to chimeric genes that comprise nucleic acid fragments as described above, the chimeric genes operably linked to at least one suitable regulatory sequence, wherein expression of the chimeric genes results in altered levels of the encoded proteins in transformed host cells.

In a further embodiment, the instant invention concerns a recombinant host cell comprising in its genome a chimeric gene encoding a soybean ARF protein, operably linked to at least one suitable regulatory sequence, wherein expression of the chimeric gene results in production of altered levels of soybean ARF protein in the transformed host cell. The transformed host cells can be of eukaryotic or prokaryotic origin. The invention also includes transformed plants that arise from transformed host cells of higher plants (either monocots or dicots), and from seeds derived from such transformed plants and subsequent progeny.

An additional embodiment of the instant invention concerns a method of altering the level of expression of a plant ARF protein in a host cell, the method comprising the steps of (a) transforming a host cell with the chimeric gene encoding a soybean ARF protein, operably linked to at least one suitable regulatory sequence; and (b) growing the transformed host cell under conditions that are suitable for expression of the chimeric gene wherein expression of the chimeric gene results in production of altered levels of a plant ARF protein in the transformed host cell.

In an alternate embodiment, the present invention provides methods of isolating a nucleic acid fragment encoding all or substantially all of the amino acid sequence encoding an ARF protein comprising either hybridization or primer-directed amplification methods known in the art and using the above described nucleic acid fragments. A primer-amplification-based method uses SEQ ID NO:1. The product of these methods is also part of the invention.

An additional embodiment of the instant invention concerns a method of identifying crop protection chemicals, the method comprising the steps of (a) contacting a transformed host cell comprising in its genome a chimeric gene encoding a soybean ARF protein, operably linked to at least one suitable regulatory sequence with a chemical compound; and (b) detecting the change in growth of the host relative to an untransformed cell. One host cell of this method is identified as ATCC 98565.

In a further embodiment, the instant invention concerns a method of identifying crop protection chemicals, the method comprising the steps of (a) contacting a plant with a chemical compound; (b) growing the plant produced in step (a) under conditions that are suitable for growth; and (c) detecting the change in the levels of ARF protein of the plant from step (b) relative to the expression levels of an untreated plant.

In another embodiment, the instant invention concerns a method of producing a transgenic plant, transgenic plant cell or transgenic plant tissue having greater resistance to the damaging effects of herbicides than a corresponding parental or non-transgenic plant, plant cell or plant tissue, the method comprising the steps of (a) stably transforming a plant ARF protein into a plant cell to produce a transgenic plant cell; (b) optionally regenerating a transgenic plant from the transgenic plant cell of step (a); and (c) growing the transgenic plant, transgenic plant cell or transgenic plant tissue under conditions which allow the expression of the ARF protein, whereby the expression of the ARF protein has the result that herbicide resistance is expressed. A transgenic plant produced by this method and the progeny of such a plant are also part of the invention.

BRIEF DESCRIPTION OF THE SEQUENCE DESCRIPTIONS AND BIOLOGICAL DEPOSIT

The invention can be more fully understood from the following detailed description and the accompanying sequence descriptions which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (2):345–373 (1984) which are herein incorporated by reference. The symbols and format used for nucleotide and amino acid sequence data comply with the rules set forth in 37 C.F.R. §1.822.

SEQ ID NO:1 is the nucleotide sequence comprising the cDNA insert in clone pBM33 encoding a soybean ARF.

SEQ ID NO:2 is the deduced amino acid sequence of the nucleotide sequence comprising the cDNA insert in clone pBM33.

SEQ ID NO:3 is the nucleotide sequence comprising the coding region of a soybean ARF protein in clone pBM33.

SEQ ID NO:4 is a sense primer used for expression of ARF protein into the ligation independent cloning pET30 vector and nucleotides 13–34 of this primer correspond to nucleotides 42–63 of SEQ ID NO: 1.

SEQ ID NO:5 is an antisense primer used for expression of ARF protein into the ligation independent cloning pET30 vector.

Applicants have made the following biological deposit under the terms of the Budapest Treaty on the International Recognition of the Deposit of Micro-organisms for the Purposes of Patent Procedure:

| Depositor Identification Reference | International Depository Designation | Date of Deposit |
|---|---|---|
| *Escherichia coli* DPD 1682 | ATCC 98565 | 30 October 1997 |

As used herein, "ATCC" refers to the American Type Culture Collection International Depository located at 12301 Parklawn Drive, Rockville, Md. 20852 U.S.A. The "ATCC No." is the accession number to cultures on deposit with the ATCC.

DETAILED DESCRIPTION OF THE INVENTION

This invention relates to the isolation of nucleic acid fragments from soybean that encode ADP ribosylation factor (ARF) protein. These proteins may be involved in the protection of plants and seeds from the damaging effects of herbicides. Plant ARF genes may be used to create transgenic plants that are capable of conferring herbicide tolerance. The invention can be used to screen chemical compounds for crop protection chemicals.

In the context of this disclosure, a number of terms and abbreviations are used.

"Adenosine diphosphate" will be abbreviated as ADP.

"ADP ribosylation factor" will be abbreviated as ARF.

An "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

"Substantially similar" refers to nucleic acid fragments wherein changes in one or more nucleotide bases result in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the instant invention (such as deletion or insertion of one or more nucleotide bases) that do not substantially affect the functional properties of the resulting transcript vis-à-vis the ability to mediate alteration of gene expression by antisense or co-suppression technology or alteration of the functional properties of the resulting protein molecule. The invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determining retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A "substantial portion" refers to an amino acid or nucleotide sequence which comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST Basic Local Alignment Search Tool; Altschul et al., *J. Mol.Biol.* 215:403–410 (1993); see also www.ncbi.nlm.nih.gov/BLAST/). In general, a sequence often or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for the purpose known to those skilled in the art. Accordingly, the instant invention comprises the complete sequences as reported in the accompanying Sequence Listing, as well as substantial portions of those sequences as defined above.

The term "complementary" describes the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the ARF protein as set forth in SEQ ID NO:2. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. An "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (*Biochemistry of Plants* 15:1–82 (1989)). It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner et al., *Mol. Biotech.* 3:225 (1995).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671–680 (1989).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet and has an effect on cellular processes.

The term "operably linked" refers to the association of nucleic acid sequences on a single nucleic acid fragment so that the function of one is affected by the other. For example, a promoter is operably linked with a coding sequence when it affects the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product (s) in organisms in amounts or proportions that differ from that of normal, wild-type, or non-transformed organisms. Production may be more specifically described as "elevated" or "decreased" relative to that of normal, wild-type, non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al., *Meth. Enzymol.* 143:277 (1987)) and particle-accelerated or "gene gun" transformation technology (Klein et al., *Nature, London* 327:70–73 (1987); U.S. Pat. No. 4,945,050).

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, (1989); (hereinafter "Maniatis").

"Crop Protection Chemicals" are chemical compounds or elements that function as insecticides, fungicides, herbicides, repellants, attractants, defoliaments, plant growth regulators, fertilizers, bactericides, micronutrients, and trace elements.

Applicants provide the sequence to the soybean ARF gene. A genetic screen for soybean proteins capable of conferring herbicide tolerance to chlorimuron-ethyl yielded sixteen colonies. Sequencing of the sixteen plasmids and comparison of the cDNA sequences to the GenBank database using the BLAST algorithms determined that five of the colonies contained plasmids encoding ARF (see Example 1, infra). The complete sequence of one of these clones (pBM33) is provided in SEQ ID NO:1, and the deduced amino acid sequence is provided in SEQ ID NO:2. ARF genes from other plants can now be identified by comparison of random cDNA sequences to the soybean ARF sequence provided herein. The ARF genes may be used to create transgenic plants that are resistant to the damaging effects of herbicides.

The instant invention used chlorimuron-ethyl. However, the genetic screen for soybean proteins capable of conferring herbicide tolerance could have been completed with any sulfonylurea herbicide. Illustrative sulfonylureas include 2-[3-(4,6-dimethylpyrimidin-2-yl)ureidosulphonyl]benzoic acid, 1-(2-chlorophenylsulphonyl)-3-(4-methoxy-6-methyl-1,3,5-triazin-2-yl)urea, methyl 2-[[[[4-methoxy-4-methyl-1, 3,5-triazin-2-yl)amino]carbonyl]-amino]sulfonyl]-benzoate, and ethyl 2-[(4-chloro-6-methoxy-pyrimidin-2-yl)amino]-arbonyl]amino]sulfonyl]-benzoate. Among them, chlorimuron-ethyl (ethyl 2-[(4-chloro-6-methoxy-pyrimidin-2-yl)amino]-arbonyl]amino]sulfonyl]-benzoate) is preferred.

The nucleic acid fragments of the instant invention may be used to isolate cDNAs and genes encoding a homologous ARF from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction or ligase chain reaction).

For example, ARF genes, either as cDNAs or genomic DNAs, could be isolated directly by using all or a portion of the instant nucleic acid fragment as DNA hybridization probes to screen libraries from any desired plant employing methodology well known to those skilled in the art. Specific oligonucleotide probes based upon the instant ARF sequence can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragment may be used in polymerase chain reaction protocols to amplify longer nucleic acid fragments encoding homologous ADP ribosylation genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant ARF. Alternatively, the second primer sequence may be based upon sequences derived from the cloning vector. For example, the skilled artisan can follow the RACE protocol (Frohman et al., *Proc. Natl. Acad. Sci., USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *Proc. Natl. Acad. Sci., USA* 86:5673 (1989); Loh et al., *Science* 243:217 (1989)). Products generated by the 3' and 5' RACE procedures can be combined to generate full-length cDNAs (Frohman et al., *Techniques* 1:165 (1989)).

Finally, availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner et al., *Adv. Immunol.* 36:1 (1984); Maniatis).

The nucleic acid fragments of the instant invention may be used to create transgenic plants in which soybean ARF may be present at altered (higher or lower) levels than normal or in cell types or developmental stages in which it is not normally found. Higher levels of ARF protein could confer herbicide tolerance in plants and seeds.

Overexpression of soybean ARF may be accomplished by first constructing a chimeric gene in which the ARF coding region is operably linked to at least one promoter capable of directing expression of a gene in the desired tissues at the desired stage of development. For convenience, the chimeric gene may comprise promoter sequences and translation leader sequences derived from the same genes. 3' Non-coding sequences encoding transcription termination signals must also be provided. The instant chimeric gene may also comprise one or more introns in order to facilitate gene expression.

A plasmid vector comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the ARF protein to different cellular compartments or to facilitate its secretion from the cell. Therefore, the chimeric gene described above may be further supplemented by altering the coding sequences to encode ARF with appropriate intracellular targeting sequences such as transit sequences (Keegstra et al., *Cell* 56:247–253 (1989)), signal sequences or sequences encoding endoplasmic reticulum localization (Chrispeels et al., *Ann. Rev. Plant Phys. Plant Mol. Biol.* 42:21–53 (1991)), or nuclear localization signals (Raikhel et al., *Plant Phys.* 100:1627–1632 (1992)) added and/or with targeting sequences that are already present removed. While the references cited give examples of each of these, the list is not exhaustive and more targeting signals of utility may be discovered in the future. It may also be desirable to reduce or eliminate expression of the ARF gene in plants for some applications. In order to accomplish this, a chimeric gene designed for co-suppression of ARF can be constructed by linking the genes or gene fragments encoding the enzymes to plant promoter sequences. Alternatively, chimeric genes designed to express antisense RNA for all or part of the ARF can be constructed by linking the ARF gene or gene fragment in reverse orientation to plant promoter sequences. Either the co-suppression or antisense chimeric genes could be introduced into plants via transformation wherein expression of the corresponding endogenous ARF gene is reduced or eliminated.

The ARF protein produced in heterologous host cells, particularly in the cells of microbial hosts, can be used to prepare antibodies to the proteins by methods well known to those skilled in the art. The antibodies are useful for detecting the soybean ARF protein in situ in cells or in vitro in cell extracts. Preferred heterologous host cells for production of soybean ARF protein are microbial hosts. Microbial expression systems and expression vectors containing regulatory sequences that direct high level expression of foreign proteins are well known to those skilled in the art. Any of these could be used to construct chimeric genes for production of soybean ARF. These chimeric genes could then be introduced into appropriate microorganisms via transformation to provide high level expression of soybean ARF protein. Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the genes encoding the ARF protein in the desired host cell, are numerous and familiar to those skilled in the art. Virtually any promoter capable of driving these genes is suitable for the present invention including, but not limited to, CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia), and lac, trp, $\lambda P_L$, $\lambda P_R$, T7, tac, and trc (useful for expression in *E. coli*).

Termination control regions may also be derived from various genes native to the preferred hosts. Optionally, a termination site may be unnecessary, however, it is most preferred if included.

Additionally, the soybean ARF protein may be used in a genetic screen to identify compounds that may be useful as crop protection chemicals. The instant invention relates to the soybean ARF protein, which is capable of conferring herbicide tolerance to chlorimuron-ethyl, one of a group of sulfonylurea herbicides.

All or a portion of the nucleic acid fragments of the instant invention may also be used as probes for genetically and physically mapping the genes that they are a part of, and as markers for traits linked to expression of soybean ARF. Such information may be useful in plant breeding in order to develop lines with desired phenotypes.

For example, the instant nucleic acid fragments may be used as a restriction fragment length polymorphism (RFLP) marker. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., *Genomics* 1:174–181 (1987)) in order to construct a genetic map. In addition, the nucleic acid fragment of the instant invention may be used to probe Southern blots containing restriction endonuclease-treated genomic DNAs of a set of individuals representing parent and progeny of a defied genetic cross. Segregation of the DNA polymorphisms is noted and used to calculate the position of the instant nucleic acid sequence in the genetic map previously obtained using this population (Botstein et al., *Am.J.Hum.Genet.* 32:314–331 (1980)).

The production and use of plant gene-derived probes for use in genetic mapping is described by Bematzky and Tanksley (*Plant Mol.Biol.Reporter* 4:37–41 (1986)). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al., *Nonmammalian Genomic Analysis: A Practical Guide,* pp. 319–346, Academic Press (1996), and references cited therein).

In another embodiment, nucleic acid probes derived from the instant nucleic acid sequences may be used in direct fluorescence in situ hybridization (FISH) mapping. Although current methods of FISH mapping favor use of large clones (several to several hundred kb), improvements in sensitivity may allow performance of FISH mapping using shorter probes.

A variety of nucleic acid amplification-based methods of genetic and physical mapping may be carried out using the instant nucleic acid sequences. Examples include allele-specific amplification, polymorphism of PCR-amplified fragments (CAPS), allele-specific ligation, nucleotide extension reactions, Radiation Hybrid Mapping and "Happy Mapping" (Dear and Cook, Nucleic Acids Research, Vol. 17, No. 17 (1989), 6795–6807). For these methods, the sequence of a nucleic acid fragment is used to design and produce primer pairs for use in the amplification reaction or in primer extension reactions. The design of such primers is well known to those skilled in the art. In methods using PCR-based genetic mapping, it may be necessary to identify DNA sequence differences between the parents of the mapping cross in the region corresponding to the instant nucleic acid sequences. This, however, is generally not necessary for mapping methods. Such information may be useful in plant breeding in order to develop lines with desired phenotypes.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Example 1

Composition of a Soybean cDNA Library with Resistance to Chorimuron-ethyl; Isolation, Sequencing and Identification of cDNA Clones

*E. coli* strain DPD 1682 [ara-14 ilvl614 ilvH612 lambda-glyA18 relA1 spoT1 ilvB619 bglR20 rbs-5::Tn5 ilvG468 (IlvG+) thi-1 tolC::miniTn10] cells (ATCC 98565) were made electrocompetent and transformed with a plasmid DNA library (see below) using a Electrocell Manipulator ECM 600 electroporation system (BTX, San Diego, Calif.). This strain of *E. coli* has had both endogenous acetolactate synthetase genes inactivated as well as tolC mutation (which allows the accumulation of sulfonylureas); the net effect is extreme sensitivity to sulfonylureas. Concentrations of 1 nM of chlorimuron-ethyl are usually lethal to this strain of *E. coli*. A lambda phage library constructed from mRNA isolated from soybean (Glycine max) leaves was purchased from Stratagene (La Jolla, Calif.) and from this library a plasmid DNA library was obtained using mass excision according to the manufacture's instructions. After electroporation, cells were plated on M9 minimal media supplemented with 0.1% glucose, 1 µg/mL thiamin, 1 mM glycine, 0.1 mg/mL carbenicillin, 1 mM isopropylthio-B-galactoside and 1 nM chlorimuron-ethyl. Plates were incubated for 6 days at room temperature. 25 colonies were selected for rescreening. Sixteen of the colonies were resistant to 1 nM chlorimuron-ethyl. Plasmid DNA was isolated from these colonies and transformed back in the original DPD 1682 strain and retested for the ability to confer clorimuron-ethyl resistance. Additionally, plasmid DNA was purified using QIAFilter cartridges (Qiagen, Chatsworth, Calif.) according to the manufacturer's instructions. The plasmid DNA was sequenced on a 391 DNA Synthesizer (ABI Inc.) using dye terminator technology and a vector specific primer.

The generated soybean sequences were identified by conducting a BLAST (Basic Local Alignment Search Tool;

Altschul et al., *J. Mol. Biol.* 215:403–410 (1993); see also www.ncbi.nlm.nih.gov/BLAST/) search for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The soybean cDNA sequences obtained were analyzed using the BLASTN algorithm provided by the National Center for Biotechnology Information (NCBI). In addition, the DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Five of the sixteen clones were identified as having homology to ARF protein. The complete sequence of one of these clones (pBM33, SEQ ID NO:1) was determined using a combination of vector and insert-specific primers. Sequence editing was performed using DNAStar (DNAStar Inc., Madison, Wis.). The sequence represents coverage at least two times in both directions.

The BLASTX search using pBM33 (SEQ ID NO:1) revealed similarity of the protein encoded by the cDNA to *Arabidopsis thaliana* (GenBank Accession No. P36397; pLog=119.244) ADP-ribosylation factor (ARF) protein. SEQ ID NO:1 shows the nucleotide sequence comprising the cDNA insert of clone pBM33 encoding a soybean ARF. The corresponding amino acid sequence of the soybean ARF is shown in SEQ ID NO:2. The amino acid sequence of the instant soybean ARF shows approximately 99.4% sequence identity to the *Arabidopsis thaliana* enzyme. Sequence alignments and BLAST scores and probabilities indicate that the instant nucleic acid fragment encodes for ARF protein.

Example 2

Elevated Levels of ARF in Soybean Seedlings Treated with Chlorimuron-ethyl

DNA from pBM33 was amplified using direct link PCR and blotted onto Hybond N+ filters (Amersham). Soybeans (cv Williams 82) were germinated in vermiculite in a controlled growth room at 23° C. with 14-h light/10-h dark cycle at 330 $\mu E\ m^{-2}\ s^{-1}$. One week old seedlings were treated with 2.5 ppm chlorimuron-ethyl or water (as a control). Seedlings were excised with a razor blade at soil level and placed into a vial containing chlorimuron-ethyl in an aqueous solution. After 24 h, leaf tissue was collected and mRNA was extracted using TriZol (GibcoBRL, Bethesda, Md.) according to the manufacture's instruction. mRNA was purified using the PolyATtract mRNA Isolation Systems (Promega, Madison, Wis.) and cDNA was synthesized using oligo dT as a primer using the Superscript Preamplification System for First Strand cDNA Synthesis (GibcoBRL) and purified away from cold nucleotides using the QIAquick nucleotide removal kit (Qiagen). DNA was then labeled with 33P dCTP using the RadPrime DNA labeling system (GibcoBRL). The radioactive probe was boiled for 5 min in 125 $\mu L$ of formamide mix (75% formamide, 1% SDS, 2.5 mg/mL salmon sperm DNA). Filters were prehybridized at 65° C. for 2 h in hybridization solution (1 M NaCl, 50 mM Tris pH 7.5, 1% SDS, 5% dextran sulfate). The boiled probe was added to prehybridized filters and allowed to hybridize for greater than 16 h in a rotisserie oven. Filters were washed with solution 1 (2×SSPE, 0.1% SDS) for 30 min at 65° C. and subsequently washed twice with solution 2 (0.5×SSPE, 0.1% SDS) before being wrapped in Mylar film and exposed 3 days to a Phosphor Imager (Molecular Dynamics). The ARF encoding message was elevated in soybean seedlings treated with chlorimuron-ethyl as compared to control seedlings.

Example 3

Expression of Chimeric Genes Encoding Soybean ARF Proteins in Maize Cells (Monocotyledon)

A chimeric gene comprising cDNA encoding a soybean ARF protein in sense orientation can be constructed by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a 100 $\mu L$ volume in a standard PCR mix consisting of 0.4 mM of each oligonucleotide and 0.3 pM of target DNA in 10 mM Tris-HCl, pH 8.3, 50 mM KCl, 1.5 mM MgCl$_2$, 200 mM dGTP, 200 mM dATP, 200 mM dTTP, 200 mM dCTP and 0.025 unit DNA polymerase. Reactions are carried out in a Perkin-Elmer Cetus Thermocycler™ for 30 cycles comprising 1 min at 95° C., 2 min at 55° C. and 3 min at 72° C., with a final 7 min extension at 72° C. after the last cycle. The amplified DNA is then digested with restriction enzymes NcoI and SmaI and fractionated on a 0.7% low melting point agarose gel in 40 mM Tris-acetate, pH 8.5, 1 mM EDTA. The appropriate band can be excised from the gel, melted at 68° C. and combined with a 4.9 kb NcoI-SmaI fragment of the plasmid pML103. Plasmid pML103 has been deposited under the terms of the Budapest Treaty with the ATCC and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega Corp., 7113 Benhart Dr., Raleigh, N.C.). Vector and insert DNA can be ligated at 15° C. overnight, essentially as described (Maniatis). The ligated DNA may then be used to transform *E. coli* XL 1-Blue (*Epicurian coli* XL-1; Stratagene). Bacterial transformants can be screened by restriction enzyme digestion of plasmid DNA and limited nucleotide sequence analysis using the dideoxy chain termination method (DNA Sequencing Kit, U. S. Biochemical). The resulting plasmid construct would comprise a chimeric gene encoding, in the 5' to 3' direction, the maize 27 kD zein promoter, a cDNA fragment encoding a plant ARF enzyme, and the 10 kD zein 3' region.

The chimeric gene so constructed can then be introduced into corn cells by the following procedure. Immature corn embryos can be dissected from developing caryopses derived from crosses of the inbred corn lines H99 and LH132 (Indiana Agric. Exp. Station, Indiana, USA). The embryos are isolated 10 to 11 days after pollination when they are 1.0 to 1.5 mm long. The embryos are then placed with the axis-side facing down and in contact with agarose-solidified N6 medium (Chu et al., *Sci. Sin.* Peking 18:659–668 (1975)). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks. The plasmid, p35S/Ac (obtained from Dr. Peter Eckes, Hoechst Ag, v Frankfurt, Germany), may be used in transformation experiments in order to provide for a selectable marker. This plasmid contains the PAT gene (see European Patent Publication 0 242 236) which encodes phosphinothricin acetyl transferase (PAT). The enzyme PAT confers resistance to herbicidal glutamine synthetase inhibitors such as phosphinothricin. The PAT gene in p35S/Ac is under the control of the 35S promoter from Cauliflower Mosaic Virus (Odell et al., Nature 313:810–812 (1985)) and the 3M region of the nopaline synthase gene from the T-DNA of the Ti plasmid of Agrobacterium tumefaciens. The particle bombardment method (Klein et al., Nature 327:70–73 (1987)) may be used to transfer genes to the callus culture cells. According to this method, gold particles (1 μm in diameter) are coated with DNA using the following technique. Ten ug of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a flying disc (Bio-Rad Labs, 861 Ridgeview Dr, Medina, Ohio). The particles are then accelerated into the corn tissue with a PDS-1000/He (Bio-Rad Labs, 861 Ridgeview Dr., Medina, Ohio), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covers a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks, the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium. Plants can be regenerated from the transgenic callus by first transferring clusters of tissue to N6 medium supplemented with 0.2 mg per liter of 2,4-D. After two weeks, the tissue can be transferred to regeneration medium (Fromm et al., Bio/Technology 8:833–839 (1990)). The expression of the ARF gene can be confirmed by analysis of the transformed maize plants by PCR, as shown in Example 2.

Example 4

Expression of Chimeric Genes in Tobacco Cells (Dicotyledon)

Cloning sites (XbaI or SmaI) can be incorporated into the oligonucleotides to provide proper orientation of the DNA fragment when inserted into the digested vector pBI121 (Clonetech Inc., 6500 Donlon Rd, Somis, Calif.) or other appropriate transformation vector. Amplification could be performed as described above and the amplified DNA would then be digested with restriction enzymes XbaI and SmaI and fractionated on a 0.7% low melting point agarose gel in 40 mM Tris-acetate, pH 8.5, 1 mM EDTA. The appropriate band can be excised from the gel, melted at 68° C. and combined with a 13 kb XbaI-SmaI fragment of the plasmid pBI121 and handled as in Example 3. The resulting plasmid construct would comprise a chimeric gene encoding, in the 5' to 3' direction, right border region, the nos promoter linked to the NPT II gene and a nos terminator region followed by a cauliflower mosaic virus 35S promoter linked to a cDNA fragment encoding a plant ARF protein and the nos terminator 3' region flanked by the left border region. The resulting plasmid could be mobilized into the Agrobacterium strain LBA4404/pAL4404 (Hoekema et al., Nature 303:179–180, (1983) using tri-parental matings (Ruvkin and Ausubel, Nature 289:85–88, (1981)). The resulting Agrobacterium strains could be then cocultivated with protoplasts (van den Elzen et al. Plant Mol. Biol, 5:149–154 (1985)) or leaf disks (Horsch et al., Science 227:1229–1231, (1985)) of Nicotiana tabacum cv Wisconsin 38 and kanamycin-resistant transformants would be selected. Kanamycin-resistant transformed tobacco plants would be regenerated. The expression of the ARF gene can be confirmed by analysis of the transformed tobacco plants by PCR, as shown in Example 2.

Example 5

Expression of Chimeric Genes in Microbial Cells and Purification of Gene Product In order to express protein, a primer designed homologous to pBM33 (SEQ ID NO:1) encoding the instant ARF protein was constructed for insertion into the ligation independent cloning (LIC) pET30 vector (Novagen, Inc., 597 Science Dr, Madison, Wis.) under the control of the T7 promoter, according to the manufacturer's instructions (see Novagen publications "LIC Vector Kits", publication number TB163 and U.S. Pat. No. 4,952,496). The sense primer was GAC GAC GAC AAG ATG AGG ATT CTG ATG GTA GGT C (SEQ ID NO:4). The antisense primer was GAG GAG AAG CCC GGT AAC GGG CCC CCC CTC GAG (SEQ ID NO:5). Amplification was performed with Advantage™ KlenTaq Polymerase mix (Clontech, Palo Alto, Calif.) with a cycle of 95° C. for 30 seconds, 55° C. for 30 sec and 72° C. for 1 min repeated for 30 cycles. The resulting band of DNA was purified using QIAquick Gel Extraction Kit (Qiagen, Chatsworth, Calif.) and annealed with pET30. The annealing reaction was transformed into NovaBlue host cells and clones with inserts were selected using agarose gel analysis. The proper clone was subsequently transformed in BL21 (DE3) host cells and used for the production of protein. The clone was grown at 37° C. in Lauria Broth to OD 600=0.6 and induced with 1 mM IPTG and allowed to grow for an additional two hours. The culture was harvested, resuspended in binding buffer, lysed with a French press and cleared by centrifugation.

Expressed protein was purified using the HIS binding kit (Novagen) according to the manufacturer's instructions. Purified protein was examined on 15–20% SDS Phast Gels (Bio-Rad Laboratories, 861 Ridgeview Dr, Medina, Ohio) and quantitated spectrophotometrically using bovine serum albumen (BSA) as a standard.

What is claimed is:

1. An isolated nucleic acid fragment encoding an ARF protein selected from the group consisting of:
   (a) an isolated nucleic acid fragment encoding the amino acid sequence set forth in SEQ ID NO:2;
   (b) an isolated nucleic acid molecule that hybridizes with (a) under the following hybridization conditions: 0.1× SSC, 0.1% SDS at 65 degrees C. for 16 h and washed with 0.5×SSPE, 0.1% SDS;
   (c) an isolated nucleic acid molecule that hybridizes with at least 20 contiguous nucleotides contained within (a);
   (d) an isolated nucleic acid fragment that is complementary to (a) or (b).

2. The isolated nucleic acid fragment of claim 1 wherein the nucleotide sequence of the fragment is set forth in SEQ ID NO:1.

3. An isolated nucleic acid fragment comprising the coding region of a soybean ARF protein wherein the nucleotide sequence of the coding region is set forth in SEQ ID NO:3.

4. A chimeric gene comprising the nucleic acid fragment of claim 1 operably linked to at least one suitable regulatory sequence.

5. A transformed host cell comprising a host cell and the chimeric gene of claim 4.

6. The transformed host cell of claim 5 wherein the host cell is a plant cell.

7. The transformed host cell of claim 5 wherein the host cell is *E. coli*.

8. A transgenic plant comprising (a) a host plant that is a monocot or a dicot and (b) the chimeric gene of claim 4.

9. A method of isolating a nucleic acid fragment encoding all or a substantial portion of the amino acid sequence encoding an ARF protein, the method comprising the steps of:
   (a) probing a cDNA or genomic library and the nucleic acid fragment of claim 1;
   (b) identifying a DNA clone that hybridizes with the nucleic acid fragment of claim 1; and
   (c) sequencing the cDNA or genomic fragment that comprises the clone identified in step (b)

wherein the sequenced cDNA or genomic fragment encodes all or a substantial portion of the amino acid sequence encoding an ARF protein.

10. The product of the method of claim 9.

11. A method of identifying crop protection chemicals, the method comprising the steps of:
   (a) contacting independently the transformed host cell of claim 5 and an untransformed host cell with a chemical compound;
   (b) detecting a change in growth rate of the transformed host cell relative to the growth rate of the untransformed host cell.

12. The method of claim 11 wherein the host cell is *E. coli* strain DPD 1682 (ATCC 98565).

13. A method of producing a transgenic plant, transgenic plant cell or transgenic plant tissue having greater resistance to the damaging effects of sulfonylurea herbicides than a non-transgenic control plant, plant cell or plant tissue, the method comprising the steps of:
   (a) stably transforming the nucleic acid of claim 1 into a plant cell to produce a transgenic plant cell;
   (b) optionally regenerating a transgenic plant from the transgenic plant cell of step (a); and
   (c) growing the transgenic plant, transgenic plant cell or transgenic plant tissue under conditions which allow expression of the ARF protein,
whereby increased expression of the ARF protein increases sulfonylurea herbicide resistance relative to a non-transgenic control plant, plant cell or plant tissue.

14. The method of claim 13 wherein the transgenic plant is a monocotyledonous or a dicotyledonous plant.

15. A transgenic plant produced by the method of claim 13 and the progeny of such a transgenic plant.

16. A method of altering the level of expression of an ARF protein in a host cell comprising; growing a transformed host cell under conditions suitable for the expression of an ARF protein, the transformed host cell comprising the chimeric gene of claim 4, wherein altered levels of a plant ARF protein in the transformed host cell relative to expression levels of an untransformed host cell are produced.

17. The method of claim 13 wherein said sulfonylurea herbicide is selected from the group consisting of 2-[3-(4, 6-dimethylpyrimidin-2-yl)ureidosulphonyl]benzoic acid, 1-(2-chlorophenylsulphonyl)-3-(4-methoxy-6-methyl-1,3,5-triazin-2-yl)urea, methyl 2-[[[[4-methoxy-4-methyl-1,3,5-triazin-2-yl)amino]carbonyl]-amino]sulfonyl]-benzoate, ethyl 2-[(4-chloro-6-methoxy-pyrimidin-2-yl)amino]-arbonyl]amino]sulfonyl]-benzoate, and chlorimuron-ethyl (ethyl 2-[(4-chloro-6-methyoxy-pyrimidin-2-yl)amino]-arbonyl]amino]sulfonyl]-benzoate).

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 950 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (iv) ANTI-SENSE: NO (vii) IMMEDIATE SOURCE:
       (B) CLONE: pBM33

(xi) SEQUENCE DESCRIPTION: SEQ ID NO:1:

| | | | | | |
|---|---|---|---|---|---|
| CTCGTGCCGA | GCTGTTCAGC | AGGTTGTTTG | CGAAGAAGGA | AATGAGGATT | CTGATGGTAG | 60 |
| GTCTCGATGC | TGCTGGTAAG | ACAACCATCT | TGTACAAGCT | CAAGCTTGGA | GAAATCGTCA | 120 |
| CCACTATCCC | CACCATCGGA | TTTAATGTTG | AGACTGTGGA | GTACAAGAAC | ATCAGCTTCA | 180 |
| CTGTGTGGGA | TGTTGGTGGT | CAGGACAAGA | TCCGTCCACT | GTGGAGGCAT | TATTTCCAGA | 240 |
| ACACTCAGGG | TCTCATTTTT | GTGGTTGATA | GCAATGATAG | AGATCGAGTG | GTTGAGGCAA | 300 |
| GGGATGAGCT | GCACAGAATG | TTGAATGAGG | ATGAACTTAG | AGATGCTGTT | TTGCTTGTTT | 360 |
| TTGCCAACAA | GCAAGATCTT | CCTAATGCAA | TGAATGCTGC | AGAAATAACT | GACAAGCTTG | 420 |
| GACTTCATTC | ACTCCGTCAA | CGCCACTGGT | ATATCCAGAG | CACTTGTGCA | ACTTCTGGAG | 480 |
| AGGGTCTCTA | TGAGGGTTTG | GACTGGCTTT | CTAACAACAT | TGCCAGCAAA | GCATGAGACA | 540 |
| TTTGAAAAAT | TTTGGTCTTG | TCTGGTGATT | TCATGCGAGT | CTGGCGGTTC | TTGGAGAAAG | 600 |
| ATGCTTATCT | TTTCTAGCGA | ATGTTGTAAT | AGCAGAATGC | TTGCTAGAAG | TATTCTCTTT | 660 |
| TGTGTAACTT | GGGTTTGTAT | GATTGCTTAA | ATTAGCTAAT | ACTTTTAGCT | ATAATTGGAA | 720 |
| CTCTTGCACC | CTCTTGTGCG | TGCGTGCTGT | GTTGCTTACA | TCTTGTTTGT | TTGATTTTTG | 780 |
| ATTGAATATA | TTTCCATGCG | TTTTGTTCTT | GAAAAGTTCA | CTAATTTTTC | AGTTTAAAAG | 840 |
| ATCGGTTTTG | TCCGGTTTTC | CAAACATTGA | TAATTAATTG | TGTAAACAAA | CTGTTGGGAC | 900 |
| TTAATTCTTA | CATTACACAG | GATTTTTATT | AAAAAAAAAA | AAAAAAAAAA | | 950 |

(2) INFORMATION FOR SEQ ID NO:2:

(i) SEQUENCE CHARACTERISTICS:
       (A) LENGTH: 175 amino acids
       (B) TYPE: amino acid
       (C) STRANDEDNESS: Not Relevant
       (D) TOPOLOGY: Not Relevant (ii) MOLECULE TYPE: protein (iii) HYPOTHETICAL: YES (iv) ANTI-SENSE: NO (xi) SEQUENCE DESCRIPTION: SEQ ID NO:2:

```
Glu Leu Phe Ser Arg Leu Phe Ala Lys Lys Glu Met Arg Ile Leu Met
1               5                   10                  15
```

Val Gly Leu Asp Ala Ala Gly Lys Thr Thr Ile Leu Tyr Lys Leu Lys
            20                  25                  30

Leu Gly Glu Ile Val Thr Thr Ile Pro Thr Ile Gly Phe Asn Val Glu
        35                  40                  45

Thr Val Glu Tyr Lys Asn Ile Ser Phe Thr Val Trp Asp Val Gly Gly
    50                  55                  60

Gln Asp Lys Ile Arg Pro Leu Trp Arg His Tyr Phe Gln Asn Thr Gln
65                  70                  75                  80

Gly Leu Ile Phe Val Val Asp Ser Asn Asp Arg Asp Arg Val Val Glu
                85                  90                  95

Ala Arg Asp Glu Leu His Arg Met Leu Asn Glu Asp Glu Leu Arg Asp
            100                 105                 110

Ala Val Leu Leu Val Phe Ala Asn Lys Gln Asp Leu Pro Asn Ala Met
            115                 120                 125

Asn Ala Ala Glu Ile Thr Asp Lys Leu Gly Leu His Ser Leu Arg Gln
        130                 135                 140

Arg His Trp Tyr Ile Gln Ser Thr Cys Ala Thr Ser Gly Glu Gly Leu
145                 150                 155                 160

Tyr Glu Gly Leu Asp Trp Leu Ser Asn Asn Ile Ala Ser Lys Ala
                165                 170                 175

(2) INFORMATION FOR SEQ ID NO:3:

(i) SEQUENCE CHARACTERISTICS:
        (A) LENGTH: 536 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vii) IMMEDIATE SOURCE:
        (A) LIBRARY: pBM33

(xi) SEQUENCE DESCRIPTION: SEQ ID NO:3:

CTCGTGCCGA GCTGTTCAGC AGGTTGTTTG CGAAGAAGGA AATGAGGATT CTGATGGTAG      60

GTCTCGATGC TGCTGGTAAG ACAACCATCT TGTACAAGCT CAAGCTTGGA GAAATCGTCA     120

CCACTATCCC CACCATCGGA TTTAATGTTG AGACTGTGGA GTACAAGAAC ATCAGCTTCA     180

CTGTGTGGGA TGTTGGTGGT CAGGACAAGA TCCGTCCACT GTGGAGGCAT TATTTCCAGA     240

ACACTCAGGG TCTCATTTTT GTGGTTGATA GCAATGATAG AGATCGAGTG GTTGAGGCAA     300

GGGATGAGCT GCACAGAATG TTGAATGAGG ATGAACTTAG AGATGCTGTT TTGCTTGTTT     360

TTGCCAACAA GCAAGATCTT CCTAATGCAA TGAATGCTGC AGAAATAACT GACAAGCTTG     420

GACTTCATTC ACTCCGTCAA CGCCACTGGT ATATCCAGAG CACTTGTGCA ACTTCTGGAG     480

AGGGTCTCTA TGAGGGTTTG GACTGGCTTT CTAACAACAT TGCCAGCAAA GCATGA        536

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Sense primer"

(iii) HYPOTHETICAL: NO

```
        (iv) ANTI-SENSE:  NO (xi) SEQUENCE DESCRIPTION:  SEQ ID NO:4:

GACGACGACA AGATGAGGAT TCTGATGGTA GGTC                                  34

(2) INFORMATION FOR SEQ ID NO:5:

(i) SEQUENCE CHARACTERISTICS:
            (A) LENGTH:  33 base pairs
            (B) TYPE:  nucleic acid
            (C) STRANDEDNESS:  single
            (D) TOPOLOGY:  linear (ii) MOLECULE TYPE:  other nucleic acid
            (A) DESCRIPTION:  /desc = "Antisense primer"

(iii) HYPOTHETICAL:  NO (xi) SEQUENCE DESCRIPTION:  SEQ ID NO:5:

GAGGAGAAGC CCGGTAACGG GCCCCCCCTC GAG                                   33
```